United States Patent [19]

Richardson et al.

[11] Patent Number: 4,822,162

[45] Date of Patent: Apr. 18, 1989

[54] METHOD AND DEVICE FOR MEASURING RETINAL RESPONSE AS A FUNCTION OF POSITION OF THE RETINA

[76] Inventors: Robert W. Richardson, 305 E. 24th St., New York, N.Y. 10010; Barbara M. Feldman, 43 Barnes St., Providence, R.I. 02906

[21] Appl. No.: 90,004

[22] Filed: Aug. 27, 1987

[51] Int. Cl.$^4$ .............................................. A61B 3/02
[52] U.S. Cl. ................................... 351/243; 351/246
[58] Field of Search ..................... 351/246, 243, 237; 128/745

[56] References Cited

PUBLICATIONS

Koblasz et al, "Wiener Kernels and Frequency Response Functions for the Human Retina", IEEE. Trans. on Biomedical Eng. 2-1980, pp. 68-75.
Kelly, D. H., "Pattern Detection and the Two-Dimensional Fourier Transform: Flickering Checkerboards & Chromatic Mechanisms" Vision Res. vol. 16, 1976, pp. 277-287.
Spraker et al, "An Electronic Checkerboard Pattern Generator for Vision Research", Electroencephalography & Clinical Neurophysiology, 1977, pp. 259-263.
Baron et al, "Component Analysis of the Foveal Local Electroretinogrqam Excited with Sinusoidal Flicker", Vision Res. vol. 19, 1979, pp. 479-490.
Marmarelis, et al, "White-Noise Analysis of a Neron Chain: An Application of the Weiner Theory", Science vol. 175, 1972, pp. 1276-1278.
Troelstra et al, "The Electrical Response of the Human Eye to Sinusoidal Light Stimulation", IEEE Trans. on Biomedical Eng. 9-1975, pp. 369-378.
Vaegan et al "Effect of Patter Luminace Profile on the Pattern ERG in Man and Pigeon", Vision Res. vol. 27 #6, 1987, pp. 883-892.
Seiple et al., Amer. J. Optom. & Physiol. Optics 63:1-6 (1986).
van Lith, et al., Dev. Ophthal. 9:133-139 (1984).
G. B. Arden and Vaegan, "Electroretinograms Evoked in Man by Local Uniform or Patterned Stimulation", J. Physiol. 341, pp. 85-104 (1983).
Curtis L. Baker, Jr. and Robert F. Hess, "Linear and Nonlinear Components of Human Electroretinogram", Journal of Neurophysiology, vol. 51, No. 5 pp. 952-967 (1984).
P. Bobak, I. Bodis-Wollner, C. Harnois, L. Maffei, L. Mylin, S. Podos and J. Thornton, "Pattern Electroretinograms and Visual-Evoked Potentials in Glaucoma and Multiple Sclerosis", Am. J. Opthal., 96, pp. 72-83 (1983).

(List continued on next page.)

Primary Examiner—Rodney B. Bovernick
Attorney, Agent, or Firm—Hamilton, Brook, Smith & Reynolds

[57] ABSTRACT

A device for detecting localized retinal damage derives focal responses of the retina from the global response of the retina to patterned stimuli in one's visual field. The stimuli comprises a series of patterns which spatially vary according to a function of a family of orthogonal functions. Each pattern also varies temporally either by being flashed before the patient or by being reversed in contrast at a fixed frequency. An electroretinogram (ERG) or magnetoretinogram (MRG) response of the patient's eye to the series of patterns is fed back into a computer generating the patterns. The responses are used by the computer to determine the coefficients of the transform of the function of the retinal response. The computer calculates the inverse transform associated with the orthogonal functions and provides the retinal response as a function of position on the retina. Contrast, intensity and temporal frequency of the patterns are chosen for a linear response of the eye. Color, intensity and temporal frequency may also be chosen to test different retinal functions. A lock-in amplifier provides the computer the signal amplitude and phase lag of the responses. A signal averager provides the computer an improved signal to noise ratio of the responses.

36 Claims, 2 Drawing Sheets

OTHER PUBLICATIONS

G. S. Brindley and G. Westheimer, "The Spatial Properties of the Human Electroretinogram", *J. Physiol.* 179, pp. 518–536 (1965).

Tatsuo Hirose, Yozo Miyake and Akira Hara, "Simultaneous Recording of Electroretinogram and Visual Evoked Response", *Arch Ophthalmology*, vol. 95, pp. 1205–1208 (Jul. 1977).

John L. Keltner and Chris A. Johnson, "Automated and Manual Perimetry—A Six Year Overview", *Ophthalmology*, vol. 91, No. 1, pp. 68–85 (Jan. 1984).

Michael A. Sandberg, Samuel G. Jacobson and Eliot L. Berson, "Foveal Cone Electroretinograms in Retinitis Pigmentosa and Juvenile Macular Degeneration", *Amer. Jrnl. of Ophthalmology*, 88:702–707, 1979.

METHOD AND DEVICE FOR MEASURING RETINAL RESPONSE AS A FUNCTION OF POSITION OF THE RETINA

BACKGROUND OF THE INVENTION

Many diseases of the eye result in localized retinal disfunction. An example of this is glaucoma in which high intraocular pressure causes damage to the nerve fiber layer of the retaina. The areas of retinal disfunction are perceived subjectively by the patient as areas of decreased reaction to light or stimulation by light as is said in the art. If the damage is such that no light, however intense, will stimulate a particular area of the retina, i.e., generate electrical activity, then that area is said to be an absolute scotoma in the patient's visual field. If the retina can be stimulated, but only by light of an intensity higher than some average predetermined baseline, then the scotoma is said to be relative.

Present methods of measuring one's visual field are purely subjective. The dimensions of one's visual field are measured in terms of visual angle, and typically measure 90° temporally and 60° nasally and vertically from a point of fixation. The standard method of measuring a patient's visual field is called Goldman perimetry. In this method one eye of the patient is patched. The eye to be tested fixates on a target spot in the middle of a hemispherical globe which has a certain constant background illumination. Visual stimuli (i.e., light) of various intensities and areas are presented in standard ways at different locations on the surface of the hemispherical globe. With the presentation of each stimulus, the patient is asked to respond by a hand signal or other means as to whether he saw the stimulus while focusing on the fixed target spot. The responses of the patient are used as measurements to determine the visual threshold at various points in the patient's visual field, thereby delineating the presence of scotomas.

An example of the utility of the Goldman perimetry technique is in the diagnosis and monitoring of glaucoma. The diagnosis of glaucoma is based on the presence of scotomas which are characteristic of the disease as well as the appearance of the optic nerve and the intraocular pressure. The visual fields of glaucoma patients are monitored closely first as an aid to making the diagnosis, and secondly to detect any progression of these visual field defects or scotomas. Any progression of the scotomas implies inadequate control of the intraocular pressure and indicates the need for additional therapy.

A problem with this technique is that it is subjective and hence subject to the judgement of the patient. Thus any inattention due, for example, to fatigue, inability to understand the test, and age degrade the quality and reliability of the test. This technique can be automated, but is still subjective and hence subject to the same vagaries.

Other techniques for testing a person's visual field have included electroretinograms (ERG's) which measure the electrical response of the entire retina to light incident upon any part of one's visual field. In order to determine the health of particular segments of the retina from the ERG responses, each spot of one's visual field must be illuminated with a focused spot of light that is flashed many times over a period of about twenty seconds. To complete such a test takes a substantial amount of time. Consequently such techniques have not shown any advantage over the subjective or other methods of testing one's visual field.

SUMMARY OF THE INVENTION

The invention described herein addresses these foregoing problems by substituting an objective measure of point-by-point retinal response for the above described subjective measure. Specifically, the present invention provides an objective method and device for examining local responses of the retina to light. A series of spatially and possibly temporally varying patterns of light intensity is presented to the eye. For each pattern, the response of the eye is measured. The patterns are chosen from a family of orthogonal functions such that each measured response corresponds to a coefficient of the transform associated with the family of orthogonal functions. The inverse transform of the transform is calculated to provide the point to point response of the retina to light stimuli.

In a preferred embodiment, a computer generates a series of patterns spatially varying in light intensities and displays the patterns before the patient on a screen. The pattern intensities spatially vary according to a function chosen from a family of orthogonal functions. The change in voltage potential across the eye, known as the electroretinogram (ERG) response of the patient's eye, to each pattern is measured by an electrode which is placed upon the patient's eye. A magnetoretinogram (MRG) or other response may also be used for this measurement. The measurements are transferred in the form of voltage signals from the electrode to a signal averager which produces an average of the responses of the eye to a particular pattern averaged over many presentations of the pattern. The signal averager improves the signal to noise ratio of the measurement signals. The averaged signal is received by the computer which relates the responses to the corresponding generated patterns and produces a set of coefficients of the transform associates with the chosen orthogonal function of the pattern. The computer then calculates the inverse transform of the transform associated with the chosen orthogonal functions and produces a map of the retinal response as a function of position over the retina.

In one embodiment of the present invention, the series of patterns are chosen to vary according to the family of sine and cosine functions. The inverse Fourier transform associated with these functions is calculated by the computer from the measured ERG voltage signal.

In addition, the series of patterns may vary in color, intensity, or contrast. By adjusting the intensity and/or contrast of the patterns, one may obtain more linear responses of the eye. The color and/or intensity can be adjusted so as to test different retinal responses.

The patterns may also vary temporally. In one mode, each pattern is presented and then reversed in contrast over time. The pattern is sinusoidally reversed back and forth at a fixed frequency. This is better known as "counter phase oscillation" at a fixed frequency. In a second mode, each pattern is presented at high intensity for a brief moment (i.e. flashed) before the patient. Both temporal modes allow signal averaging of the response of the eye to improve the signal to noise ratio. The temporal frequency may also be chosen so as to test different retinal functions or minimize the nonlinear response of the eye.

In the oscillating mode, a lock-in amplifier can be used in place of the signal averager to provide signals indicative of the voltage amplitude and phase lag of the ERG responses of the eye.

BRIEF DESCRIPTION OF THE DRAWINGS

The foregoing and other objects, features and advantages of the invention will be apparent from the more particular description of preferred embodiments of the invention, as illustrated in the accompanying drawings in which like referenced characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
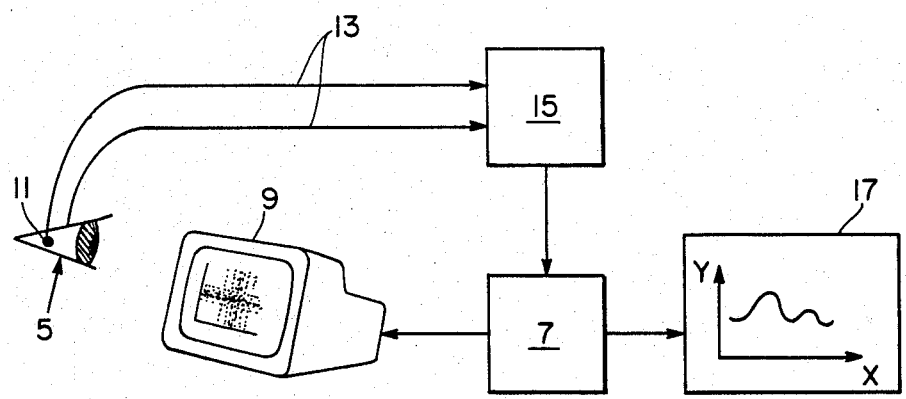
FIG. 1 is a schematic of a device embodying the present invention.

The present invention discloses a method and device for obtaining a point-by-point response of the retina, known as a focal ERG (FERG), from an ERG response of the retina. A typical ERG response ranges between 0.1 $\mu v$ to about 100 $\mu v$ where the signal strength depends upon the stimulus and state of adaption of the retina. The ERG response from a point source stimulus which subtends a small, visual, solid angle in the subject's visual field would give rise to a small signal and consequent small signal to noise ratio. Such small signals make any point-by-point observation of the retina difficult and very time consuming where the ERG response from a point source stimulus would have to be repeated and measured to each point throughout the retina in order to map the visual field. The present invention obtains point by point retinal responses (FERG's) from ERG's by analyzing a patient's global ERG responses to a series of patterns of known and controlled construction in such a way that the FERG can be derived.

In general, a set of patterns spatially varying in intensity is presented to the eye. For each pattern, the ERG response of the eye is measured. The patterns are chosen to spatially vary in intensity according to a function from a family of orthogonal functions such that each measured ERG response corresponds to a coefficient of the transform associated with the family of orthogonal functions.

For example, a first pattern spatially varies in intensity according to a function of the family of sines and cosines at a wave number $k_1$. The measured ERG response of the retina to this pattern corresponds to coefficient $c_1$ of the transform associated with this family of orthogonal functions. A second pattern spatially varies in intensity according to the same function as the first pattern but at wave number $k_2$. The measured ERG response of the retina to this pattern corresponds to coefficient $c_2$ of the transform associated with the family of sines and coines. A third and fourth pattern similarly follow and provide coefficients $c_3$ and $c_4$ respectively. This procedure can be continued with improved spatial resolution resulting from the measurement of more coefficients.

Knowing the coefficients ($c_1$, $c_2$, $c_3$, $c_4$, . . . ), the transform is determined. The spatial wave numbers $k_i$ are chosen so that the functions with different wave numbers are orthogonal. By calculating the inverse transform of the transform, point-by-point responses along the retina are obtained.

Alternatively, an MRG response may be used in place of the ERG response of the eye for each pattern. Measurement of other responses of the eye are also suitable, for example the pupilary response or the visually evoked potential of the eye. One of these or a combination of the forementioned types of measurements may be used to determine the coefficients of the pertinent transforms associated with different visual functions.

The foregoing describes the essence of the present invention and is a greatly simplified description. In practice, the measured ERG signal is not pure; that is, it includes noise. Hence other techniques are incorporated to compensate for the noise. In one technique, several ERG responses are measured for each pattern and are averaged. These averaged ERG measurements are used to define determine the coefficients of the transform.

In another noise compensation technique, each pattern is temporally varied in its presentation to the eye. The time control of the presentation of each pattern allows noise to be filtered out of the ERG response. Each pattern may be temporally varied sinusoidally or according to other pertinent functions. Alternatively, each pattern may be temporally varied in a flash mode. In the flash mode, each pattern is presented at high luminance for a brief moment. This allows repeated presentation of the same pattern with signal averaging used to improve the signal to noise ratio.

It is understood that any combination of the above described and other noise compensation techniques may be used to enhance the accuracy of the ERG response measurement and thereby the point-to-point response outcome of the present invention.

Further, different levels of intensity and/or contrast may be used in the patterns. Retinal response to the patterns may then be controlled to provide a linear response, even though the retinal response is generally non-linear. The linear regime of response is necessary in order to properly calculate the inverse transform from the transform associated with the patterns' family of orthogonal functions. The temporal frequency of the patterns may also be chosen so as to minimize the non-linear response of the eye.

The temporal frequency, color and/or intensity of the patterns may be varied so as to measure different functions of the eye. For example, rod and come functions can be distinguished by varying the color and intensity of the patterns or temporal frequency and color of the patterns, or the like.

The following describes details of the present invention incorporating noise compensation techniques in which the series of patterns is presented in a counter phase oscillation at a fixed frequency. That is, each pattern continually reverses its contrasting lines sinusoidally over time, or oscillates in contrast reversal as is said in the art, at a constant frequency. Any other modes, such as the flash mode, can be treated similarly.

Figure 2A:
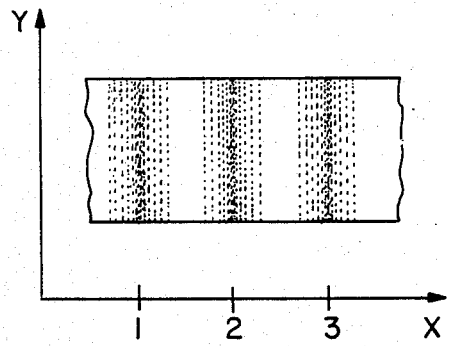
FIGS. 2a–2c are illustrations of cosinusoidally varying patterns, along the x-axis, y-axis and both axes respectively.
Figure 2B:
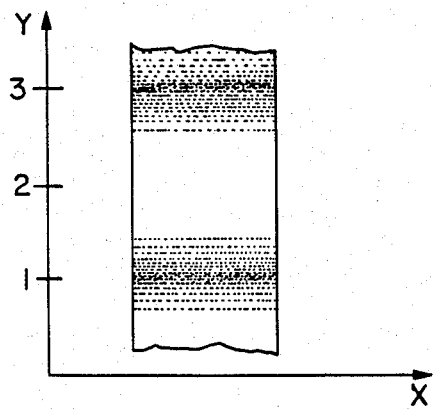
Figure 2C:
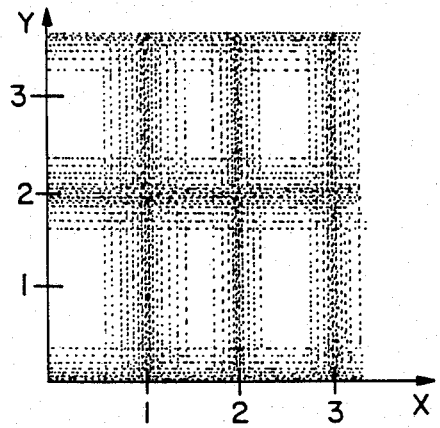

A device embodying the present invention is illustrated in FIG. 1. A computer 7 generates a series of spatially and temporally varying patterns and displays each pattern on a terminal screen 9. An example of such a display system is the Venus system from the Neuroscientific Corporation of N.Y. In particular, each pattern is spatially varying in the x or y direction or both directions according to a sine or cosine function as illustrated in FIGS. 2a–2c. FIG. 2a illustrates a pattern cosinusoidally varying in space along the x-axis at a fixed time t. The pattern progressively changes from light to dark to light from left to right. FIG. 2b illustrates cosinusoidal spatial variance in the y direction at a fixed time t. This time the pattern progressively changes from light to dark to light from bottom to top. FIG. 2c illustrates a pattern cosinusoidally varying in space along both the x and y axis at a fixed time t. Hence, the progressive changing from light to dark to light occurs both from left to right and from top to bottom. The choice of sines and cosines for the spatial variation of the patterns is one example of many different choices.

Figure 3A:
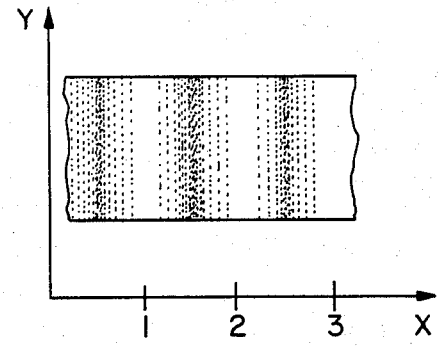
FIGS. 3a–3c are illustrations of temporal variance of the patterns of FIGS. 2a–2c respectively.
Figure 3B:
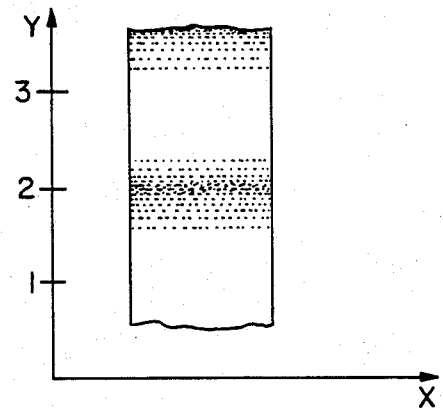
Figure 3C:
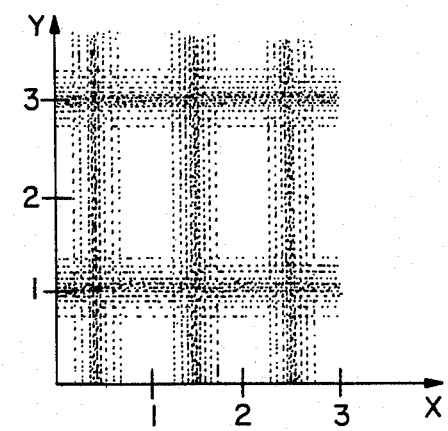

Each pattern temporally varies by sinusoidally reversing its lightly shaded areas to a dark shade and vice versa (i.e. the counter phase oscillation or contrast reversal) at some frequency f. FIGS. 3a–3c illustrate temporal variance respectively of FIGS. 2a–2c. FIG. 3a illustrates the pattern of FIG. 2a at a time $t_1$ where $t_1$ is greater than t by half a period. Note that pattern is lightest in FIG. 3a where it was darkest in FIG. 2a along the x-axis. FIG. 3b illustrates the pattern of FIG. 2b as temporally changed at time $t_1 > t$. The pattern in FIG. 3b is darkest where it was lightest in FIG. 2b along the y-axis. Similarly, FIG. 3c illustrates the pattern of FIG. 2c as temporarlly changed at time $t_1 > t$.

Figure 4:
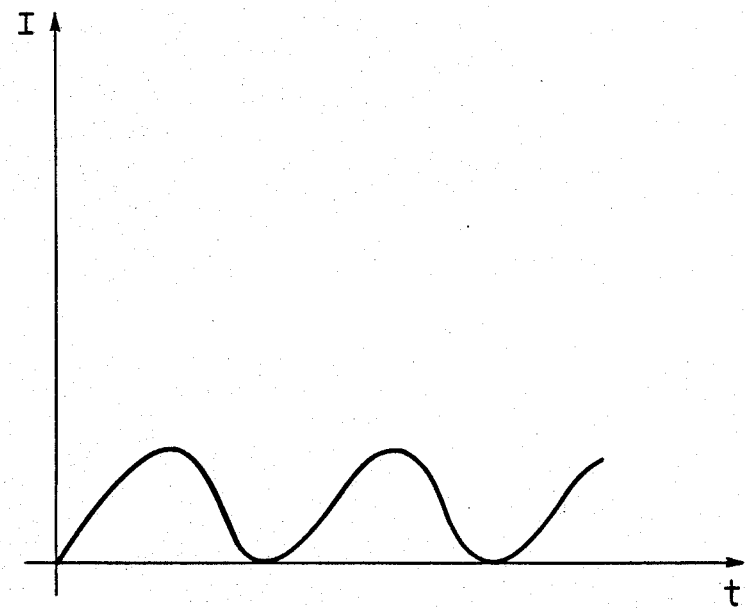
FIG. 4 is a graph of the change in intensity over time at one point on a screen displaying patterns which temporally vary sinusoidally.

FIG. 4 provides the graph of the change in intensity I over time t at one fixed position on screen 9 where the modulation of the intensity is 100%, with the illumination of the above described patterns. It is seen by the graph that the change in intensity I experienced at the one fixed position is sinusoidal. Similar sinusoidal changes in intensity with varying amounts of modulation are experienced at the other positions on screen 9.

The luminance or light intensity I at a time t for each pattern displayed on screen 9 has the form $$I(x,y,t) = I_o[1 + m \cos \omega t F_L(x,y)] \quad \text{(Equation 1)}$$

where $I_o$ is the average overall intensity;

m is modulation or peak value of the contrast between the lightest and darkest shades;

$\omega = 2\pi f$, where f is the temporal frequency of contrast reversal chosen in the range from about 1 Hz to about 60 Hz (other ranges however can be used); and $F_L(x,y)$ is the particular spatial pattern where L labels the particular choice of function from the family of orthogonal functions.

In this case, it was chosen that $$F_L(x,y) = \cos kx \cos ly$$

where x and y are coordinates of position on the screen 9; k and l are appropriate wave vectors; and L refers to the values of k, l and the fact that cosines were chosen.

After computer 7 generates a pattern constructed to the above equations, it displays the pattern on screen 9 before the patient. The retina of the patient's eye 5 responds to the display pattern (referred to in the art as a stimulus) with a characteristic length of time of about 0.1 seconds or greater. That is, the eye does not instantaneously respond. An ERG electrode 11, of the type common in the art, placed on the eye 5 produces a voltage signal when the retina responds to the pattern. The voltage signal is a measurement of the change in voltage potential across the eye and is indicative of the response of the eye to the pattern that has been displayed prior to that time.

The voltage signal is transferred through lines 13 to a signal averager 15 which is synchronized to the presentation of the patterns, stores the response, and adds future responses of the retina to the same pattern. The sum of responses is divided by the number of responses stored and added to provide an average voltage signal of the eye 5 to the particular pattern displayed. The averaging of the voltage signals serves to improve the signal-to-noise ratio in the ERG detection scheme.

The averaged voltage signal is passed to computer 7 which relates the response of the eye as indicated by the average voltage signal to the generated and displayed pattern which caused the response. That pattern, remeber, was generated and displayed at times into the past $\tau$ before the time t at which the voltage signal was received by the computer 7. The ERG voltage signal, V(t), at a time t, that is generated by the eye to the particular pattern displayed has the form:

$$V(t) = \int_0^\infty d\tau \int dX dY \, h(X,Y,\tau) \, I(X,Y,t-\tau) \quad \text{Equation 2}$$

where $\tau$ is time into the past from the time t;

X,Y are coordinates location position on the retina from the x,y positions on the screen 9;

$I(X,Y,t-\tau)$ is the light intensity of the chosen pattern as previously discussed at a time $\tau$ before the present time t; and $h(X,Y,\tau)$ is the form of the focal ERG(FERG) of the eye. That is, $h(X,Y,\tau)$ dX dY is the voltage generated at time t by a pulse of light of unit strength at time $t-\tau$ which is incident upon the small area of the retina dX dY located at the position X,Y.

Note that $h(X,Y,\tau) = 0$ for $\tau < 0$. The function $h(X,Y,\tau)$ is also known in the art as the memory function of the retina. It provides the continuing response of the retina to a stimulus presented in the past. The retina does not response instantaneously and then responds in a decreasing manner to stimuli that occurred further into the past. Hence, $h(X,Y,\tau)$ is zero at $\tau = 0$, rises to a peak, falls, and then has a decreasing value with increasing $\tau$(time into the past). More importantly, $h(x,y,\tau)$ is the FERG signal of interest that can be used to study retinal response on a point by point basis over the retina and to diagnose localized retinal disfunction. Computer 7 determines $h(X,Y,\tau)$ from the received voltage signals V(t) in the following manner.

Substituting from Equation 1 the light intensity I(x,y,t) of the chosen pattern into Equation 2, the computer 7 obtains the signal at frequency f Equation 3

-continued $$V(t) = I_o m \int_0^\infty d\tau \int dXdY\, h(X,Y,\tau) \cos\omega(t-\tau) F_L(X,Y)$$

$$= I_o m \int_0^\infty d\tau \int dXdY\, h(X,Y,\tau) [\cos\omega t \cos\omega\tau + \sin\omega t \sin\omega\tau] F_L(X,Y)$$

$$= I_o m [v_1 \cos\omega t + v_2 \sin\omega t]$$

where $\omega = 2\pi f$, $f$ is the frequency of the oscillation $$v_1 = \int_0^\infty d\tau \cos\omega\tau \int dXdY\, h(X,Y,\tau) F_L(X,Y)$$

$$v_2 = \int_0^\infty d\tau \sin\omega\tau \int dXdY\, h(X,Y,\tau) F_L(X,Y)$$

That is, $v_1$ is the in-phase response, and $v_2$ is the 90° out-of-phase response. $v_1$ and $v_2$ may be written in the form $$v_i(L,\omega) = \int dXdY\, h_i(X,Y,\omega) F_L(X,Y) \text{ for } i = 1,2 \quad \text{Equation 4}$$

where $$h_1(X,Y,\omega) = \int_0^\infty d\tau\, h(X,Y,\tau) \cos\omega\tau, \quad \text{Equation 5}$$

$$h_2(X,Y,\omega) = \int_0^\infty d\tau\, h(X,Y,\tau) \sin\omega\tau.$$

At any time t, V(t) has a known value as given to computer 7 from signal averager 15. This value is then set equal to Equation 3 in which all factors but $v_1$ and $v_2$ are known. A value for $v_1$ ($v_2$) is then obtained by multiplying V(t) by cos $\omega$t (sin $\omega$t), integrating the result over one period of the signal, and dividing the result by $I_o m\pi/\omega$. These values or amplitudes $v_1$ and $v_2$ are also proportional to the two outputs of a verctor lock-in amplifier when lock-in detection of the signal is used.

Knowing values for $v_1$ and $v_2$ the computer 7 calculates $h_i(X,Y,\omega)$. This output is sufficient for many diagnostic procedures. More detailed information can be obtained by repeating the measurement at many different frequencies f and using the Fourier theorem to construct $h(X,Y,\tau)$ from the measured dependence of $h_i(X,Y,\omega)$ upon $\omega$. Alternatively, $h(X,Y,\tau)$ can be measured directly if the stimulus is flashed temporally.

According to the generalized Fourier Theorem $$h_i(X,Y,\omega) = \sum_L \bar{h}_i(L,\omega) F_L(X,Y) \frac{1}{A_L},$$

where the orthogonal functions $F_L$ satisfy $$\int dXdY F_L(X,Y) F_{L'}(X,Y) = A_L \delta_{LL'},$$

where $A_L$ is a normalization factor; $\delta$ is a Kronecker delta; and $\bar{h}_i$ is given by $$\bar{h}_i(L,\omega) = \int dXdY h_i(X,Y,\omega) F_L(X,Y).$$

Thus, from Equation 4, $\bar{h}_i(L,\omega) = v_i(L,\omega)$ and $h_i(X,Y,\omega)$ can be determined from the measured values of $v_i(L,\omega)$.

That is, the subject's FERG can be constructed from his ERG responses to many spatial patterns of stimulus.

In the flash mode of temporal presentation of the stimulus, the luminance pattern, Equation 1, is given by $$I(x,y,t) = I_0[1 + m\delta(t-t_0) F_L(x,y)],$$

where $\delta(t-t_0)$ is a Dirac delta function representing a brief but intense flash of the pattern $F_L$ at time $t_o$ which is repeated many times. The temporally varying ERG voltage in response to this stimulus is $$V(t) = I_o m v(L,t),$$

where $$v(L,t) = \int dXdY h(X,Y,t-t_0) F_L(X,Y).$$

Thus, in this case $$h(X,Y,t-t_0) = \sum_L v(L,t) F_L(x,y) \frac{1}{A_L}$$

and the full temporal behavior of h is determined.

As an example of this technique, the applicants consider a subject's FERT at the fixed frequency f with a rectangular spatial pattern and products of sines and cosines for the functions $F_L$. Applicants then have $-X_o < X < X_o$ and $-Y_o < Y < Y_o$ where X (Y) is interpreted as the subject's visual angle measured horizontally (vertically) from the point of fixation. $X_o$ and $Y_o$ determine the extent of the spatial pattern in the subject's visual field. The spatial patterns $F_L(x,y)$ are now specified in detail and are given by $$F_{p,q}^{(r,s)}(X,Y) = f_p^{(r)}(X) g_q^{(s)}(Y) \quad \text{Equation 6}$$

where $$f_p^{(1)}(X) = \cos(k_p X),\; g_q^{(1)}(Y) = \cos(l_q Y),$$

$$f_p^{(2)}(X) = \sin(k_p X),\; g_q^{(2)}(Y) = \sin(l_q Y),$$

$$k_p = \frac{\pi p}{X_o}; \; l_q = \frac{\pi q}{Y_o}; \; r,s = 1,2 \text{ and } p,q = 0,1,2,3 \dots$$

Examples of these patterns are given in FIGS. 2 and 3. With this choice of function $A_{o,q} = A_{p,o} = 2X_o Y_o$ and $A_{p,q} = X_o Y_o$ for p,q = 1,2 . . . Applicants exclude the pattern with p=q=o since that entails a net luminance change and stimulates a process in the retina that is different from the other patterns whose net luminance is constant in time. If $v_i^{(r,s)}(p,q,)$ is the in-phase, i=1 or cut-of phase, i=2, ERG voltage in response to this stimulus, then $$h_i(X,Y,\omega) = \sum_{p,q} \sum_{r,s} v_i^{(r,s)}(p,q,) f_p^{(r)}(X) g_q^{(2)}(Y) \frac{1}{A_{p,q}}. \quad \text{Equation 7}$$

This is desired FERG as a function of retinal position X Y. Since in practice only a finite number of terms are included in the sums over p and q, this is, in the sense of the Fourier theorem, a least squares fit to the function $h_i$.

The angular resolution of the FERG on the retina is determined by the number of different patterns used. The angular resolution of the FERG in the horizontal (vertical) direction will be equal to the width (height) of the patterns divided by the number of different values of $k_p(l_q)$ in F(x,y) in Equation 6. Thus, for a 40×40 degree pattern and a total of twenty different values of $k_p$ and $l_q$, the FERG will be measured with a 2×2 degree spatial resolution. Spurious spatial signals can be eliminated by averaging $h_i$ over an appropriate window. Thus, if $W_x(X,X')$ and $W_y(Y,Y')$ are the chosen X- and Y- windows then the smoothed output is $$\bar{\bar{h}}_1(X,Y,) = \int dX' dY' W_x(X,X') W_y(Y,Y') h_i(X',Y',\omega).$$

If we use square windows of widths $2x_o$ and $2y_o$ in the x- and y- directions, then this amounts to multiplying $f_p^{(r)}$ by $\sin(k_p x_o)/(k_p x_o)$ and $g_q^{(s)}$ by $\sin(l_q y_o)/(l_q y_o)$. This eliminates noise with a high spatial frequency and improves the convergence of the Fourier expansion.

Although, the eye naturally responds in a non-linear fashion, the modulation m and temporal freqency f in Equation 1 can be adjusted such that the eye responds in a more linear fashion as detected by ERG electrode 11.

If a lock-in amplifier is used in place of signal averager 15, values for $v_1$ and $v_2$ in Equation 3 may be obtained directly. This is accomplished by the lock-in amplifier measuring and providing the amplitude A of the ERG voltage and the phase lag of the eye response where $$V(t) = I_o m[v_1 \cos \omega t + v_w \sin \omega t] \qquad \text{(Equation 3)}$$

and $$V(t) = A \cos(\omega t + \omega) = A[\cos \phi \cos \omega t - \sin \phi \sin \omega t]$$

so $$I_o m v_1 = A \cos \phi;$$

and $$I_o m v_2 = -A \sin \phi.$$

It is understood that the spatially varying patterns may be chosen to follow any orthogonal function of the family of orthogonal functions which forces a set of eye responses to define a transform of the retinal responses in the frequency domain and enable calculation of the inverse transform, of the defined transform associated with that function, to obtain the spatial domain of the retinal response.

For example, $F_L(x,y)$ in Equation 1 could have been chosen to be $$F_L(x,y) = \cos m\phi J_o(\gamma_n r/r_o) = \sin m\phi J_o(\gamma_n r/r_o),$$

where $J_o$ is a Bessel function and $\delta_n$ is the $n^{th}$ root of $J_o(\gamma) = 0$. $\phi$ is the azimuthal angle. The indices range is $m = 0, 1, \ldots$ and $n = 1, 2, \ldots$ The angular radius of the screen 9 is $r_o$. In this case, the spatial Fourier transform and associated inverse Fourier transforms of the Bessel junction $J_o$ are used to calculate $h(X,Y,\tau)$ from the measured voltage signals $V(t)$ of the ERG electrode 11.

While the invention has been particularly shown and described with reference to embodiments thereof, it will be understood by those skilled in the art that various changes in form and detailed may be made therein without departing from the spirit and scope of the invention as defined by the appended claims.

We claim:

1. A method of measuring retinal response of an eye, the steps comprising:
presenting a series of patterns of spatially varying light intensity, the patterns chosen from a family of orthogonal functions;
measuring, for each pattern, response of the eye such that the responses provide a set of coefficients of a transform associated with the family of orthogonal functions; and
computing an inverse transform of the transform associated with the family of orthogonal functions to provide a spatial retinal response as a function of position over the retina.

2. A method as claimed in claim 1 wherein the step of presenting a series of varying patterns further includes presenting a series of temporally varying patterns.

3. A method as claimed in claim 2 wherein the temporal frequency for each pattern is at a predefined fixed frequency from the range of about 1 to about 60 Hz.

4. A method as claimed in claim 2 wherein the temporal frequency is chosen so as to minimize nonlinear response of the eye.

5. A method as claimed in claim 2 wherein the temporal frequency is chosen so as to test different retinal functions.

6. A method as claimed in claim 2 wherein each pattern is presented repeatedly for only a brief moment of time.

7. A method as claimed in claim 1 wherein the step of measuring response of the eye includes measuring an electroretinographic voltage potential across the eye.

8. A method as claimed in claim 1 wherein the step of measuring response of the eye includes obtaining a magnetoretinographic response of the eye.

9. A method as claimed in claim 1 wherein the step of measuring response of the eye includes obtaining pupilary response of the eye.

10. A method as claimed in claim 1 wherein the step of measuring response of the eye includes obtaining a visual evoked potential of the eye.

11. A method as claimed in claim 1 wherein the step of measuring response of the eye includes obtaining a combination of different types of response measurements of the eye.

12. A method as claimed in claim 1 wherein the series of patterns are chosen to vary according to a family of sinusoidal functions.

13. A method as claimed in claim 1 wherein the series of patterns are chosen to vary according to a family of Bessel functions.

14. A method as claimed in claim 1 wherein the step of presenting a series of patterns of spatially varying intensity further includes presenting a series of patterns having colors chosen to test different retinal functions.

15. A method as claimed in claim 1 wherein the step of presenting a series of patterns further includes presenting a series of patterns having an intensity chosen to test different retinal functions.

16. A method as claimed in claim 1 wherein the step of presenting a series of patterns of spatially varying intensity further includes adjusting contrast of the patterns to obtain linear responses of the eye.

17. A method as claimed in claim 1 further comprising the step of adjusting the intensity to obtain a linear response of the eye.

18. A device for measuring retinal response of an eye comprising:
means for presenting to the eye a series of patterns spatially varying in intensity, the variation being chosen from a family of orthogonal functions;
means for measuring, for each pattern, response of the eye, said means providing signals indicative of the responses of the eye; and calculation means responsive to the signals in a manner which relates the signal indicated responses to the corresponding patterns, so as to provide a set of coefficients of a transform associated with the chosen orthogonal function, and subsequently compute an inverse transform of the transform associated with the chosen orthogonal function to provide a spatial retinal response of the eye as a function of position over the retina.

19. A device as claimed in claim 18 wherein the patterns further vary temporally at a temporal frequency.

20. A device as claimed in claim 19 wherein the temporal frequency is a fixed predefined frequency between about 1 Hz and about 60 Hz.

21. A device as claimed in claim 19 wherein the temporal frequency is chosen so as to minimize nonlinear response of the eye.

22. A device as claimed in claim 19 wherein the temporal frequency is chosen so as to test different retinal functions.

23. A device as claimed in claim 19 wherein the series of patterns are repeatedly flashed for a brief moment before the eye.

24. A device as claimed in claim 18 wherein the means for measuring includes an electrode connected to the eye for providing a electroretinographic voltage potential across the eye.

25. A device as claimed in claim 18 wherein the means for measuring include an electronic sensor of potential across the eye.

26. A device as claimed in claim 18 wherein the means for measuring include a magnetic sensor for providing a magnetoretinographic response of the eye.

27. A device as claimed in claim 18 wherein the means for measuring include means for obtaining a pupilary response of the eye.

28. A device as claimed in claim 18 wherein the means for measuring include means for obtaining a visually evoked potential of the eye.

29. A device as claimed in claim 18 wherein the series of patterns spatially vary in intensity according to a family of sine and cosine functions.

30. A device as claimed in claim 18 wherein the series of patterns spatially vary in intensity according to Bessel functions.

31. A device as claimed in claim 18 wherein the series of patterns have colors chosen so as to test different retinal functions.

32. A device as claimed in claim 18 wherein the series of patterns have an intensity chosen so as to test different retinal functions.

33. A device as claimed in claim 18 wherein contrast of the patterns is adjusted to enable linear responses of the eye.

34. A device as claimed in claim 18 wherein intensity of the patterns is adjusted to obtain linear responses of the eye.

35. A device as claimed in claim 18 further comprising a signal averager receiving the signals from the measuring means and providing the calculation means with an average of the signals for each pattern.

36. A device as claimed in claim 18 further comprising a lock-in amplifier for providing to the calculation means signals indicative of amplitude and phase lag of the responses of the eye.

* * * * *